United States Patent [19]

Bornengo

[11] 4,110,405

[45] Aug. 29, 1978

[54] ONE STEP PROCESS FOR PREPARING 2,6-DINITRO-4-TRIFLUOROMETHYL-CHLOROBENZENE BY NITRATION OF 4-TRIFLUOROMETHYLCHLOROBENZENE

[75] Inventor: Mario Bornengo, Massa, Italy

[73] Assignee: Montedison S.p.A., Milan, Italy

[21] Appl. No.: 844,410

[22] Filed: Oct. 21, 1977

[30] Foreign Application Priority Data

Oct. 22, 1976 [IT] Italy .............................. 28606 A/76

[51] Int. Cl.$^2$ ............................................. C07C 79/12
[52] U.S. Cl. .................................................... 260/646
[58] Field of Search .................. 260/646; 71/121, 125; 424/349

[56] References Cited

U.S. PATENT DOCUMENTS

| 3,586,725 | 6/1971 | Hunter | 260/646 |
| 3,984,488 | 10/1976 | Milligan | 260/646 |

*Primary Examiner*—Benjamin R. Padgett
*Assistant Examiner*—Irwin Gluck

[57] ABSTRACT

There is disclosed a one-step process for dinitrating 4-trifluoromethylchlorobenzene to obtain the 2,6-dinitro-derivative.

2 Claims, No Drawings

ONE STEP PROCESS FOR PREPARING 2,6-DINITRO-4-TRIFLUOROMETHYLCHLOROBENZENE BY NITRATION OF 4-TRIFLUOROMETHYLCHLOROBENZENE

THE PRIOR ART

The prior art describes a two-step process for the dinitration of 4-trifluoromethylchlorobenzene. In the first step, 2-nitro-4-trifluoromethylchlorbenzene is formed and isolated by vacuum distillation (b.p. 92–93° C at 10 mm Hg). In the second step the 2-nitro-4-trifluorochlorobenzene is further nitrated; see U.S. Pat. No. 2,257,093 and French Patent No. 745,293, 1932.

According to U.S. Pat. No. 2,257,093, the dinitration can be carried out in one step, but - see Example 1 of the patent — the yields are low.

According to the latest technique, 4-trifluoromethylchlorobenzene is added to a 2:1 mixture of smoking $H_2SO_4$ at 20–30% of $SO_3$ and of $HNO_3$ at 98% (density: 1.5) in molar ratios of nitrating mixture: 4-trifluoromethylchlorobenzene = 10:1, whereupon the mass is heated on a steam bath for 30 minutes. The whole is poured into water and ice and is partially neutralized with aqueous ammonia. The organic layer that separates is dried on $CaSO_4$ and distilled under vacuum. The 2-nitro-4-trifluoremethylchlorobenzene has a boiling point of 92–93° C at a residual pressure of 10 mm Hg, the yield being 75%.

The mononitroderivative so obtained is further nitrated by dissolving the 2-nitro-4-trifluoromethylchlorobenzene into twice its weight of smoking 30% sulphuric acid and by gradually adding it to a mixture composed of 20 parts of sulphuric acid and of 15 parts of 99% nitric acid (density: 1.5), in weight ratios of 2-nitro-4-trifluoromethylchlorobenzene: mixture = 1:7. The mass is heated for 3 hours to 100° C and then for 30 minutes to 105°–115° C. After a few hours rest, the whole is poured onto ice. The ice is allowed to melt, then the precipitated solid is filtered and washed with water. The yield is 85%.

According to this method (see Bekeser, J. AM. Chem. Society 74, 1952, page 3012; Yagupol'skif, Ukrain Khim. Zhur. 21, 1955, pages 81–85; H. Jurgens, J. Org. Chemistry 25, 1960, page 1719) which appears to be the most up-to-date and advanced method, the total yield is 63.8% (75% × 85%) in respect of the starting 4-trifluoromethylchlorobenzene.

The one-step dinitration without isolation of the intermediate mononitro-trifluoromethylchlorobenzene provides, in fact, a yellow-orange product that, unless it is recrystallized, rapidly changes into a brown mass which liberates nitrous vapors.

THE PRESENT INVENTION

One object of this invention is to provide an improved, one-step process for dinitrating 4-trifluoromethylchlorobenzene in the 2,6 position.

This and other objects are accomplished by the invention, in accordance with which pure 4-trifluoromethylchlorobenzene is dropped, under stirring at 50° C–60° C., into a mixture composed of 90% by weight $HNO_3$ (of density 1.483) and of sulphuric acid at 20% of $SO_3$, in a molar ratio of nitric acid to 4-trifluoromethylchlorobenzene of 4.5:1, the reaction mass is heated for 3 hours at 100° C and then for 1 hour at 110° C, with continued stirring, then allowed to rest for 3 to 4 hours, and finally mixed with ice to precipitate 2,6-dinitro-4-trifluoromethylchlorobenzene in the form of yellow needles which, after filtering, washing with cold water and drying, have a melting point of 55°–56° C. The yield, calculated on the starting 4-trifluoromethylchlorobenzene, is from 82% to 85%.

Besides permitting the achievement of a high dinitration yield, the method of this invention involves a lesser evolution of nitrous vapors ($NO \rightarrow NO_2 \rightleftarrows N_2O_4$) and smaller amounts of exhausted acids.

2,6-dinitro-4-trifluoromethylchlorobenzene can be used as an intermediate in the preparation of azo-dyestuffs (see U.S. Pat. No. 2,257,093) or of herbicides such as "Trifluralin" (2,6-dinitro-N,N-dipropyl-4-trifluoromethylaniline).

The mixture containing 90% $HNO_3$ and $H_2SO_4$ at 20% of $SO_3$ is used in weight ratios ranging from 1:5 to 1:6. The spent acid, obtained in the nitration according to the invention, can be recovered by conveying it to the denitrification towers where, by treatment with a rising stream of saturated or superheated vapor, the nitric acid distills at the top, while the denitrified sulphuric acid (at 67–70% of $H_2SO_4$) flows out from the tower bottom. The nitrous vapors that form during the nitration can be utilized, for example, to produce nitric acid.

The following Example 2 is given to illustrate the invention in more detail and is not intended to be limiting.

EXAMPLE 1 (Comparative)

Preparation of 2,6-Dinitro-4-Trifluoromethylchlorobenzene According to U.S. Pat. No. 2,257,093

180.5 g of 4-trifluoromethylchlorobenzene were dissolved in a mixture consisting of 250 g. of 100% $H_2SO_4$ and of 50 g. of smoking $H_2SO_4$ (24% of $SO_3$). The solution was cooled to 20° C and a mixture of 100 g. of 100% $H_2SO_4$ and of 70 g. of $HNO_3$ (density = 1.49) was gradually added dropwise under stirring and taking care that the temperature did not exceed 30° C. The mass was then heated to 75° C–80° C and a mixture containing 100 g. of 100% $H_2SO_4$ and 70 g. of $HNO_3$ (density = 1.49) was added dropwise. The mass was then heated to 95° C and stirred for 10 hours at that temperature, after which it was further heated to 130° C for 2 hours, and then poured onto 1500 g. of ice. The yellow-orange precipitate was recovered by filtration, washed with cold water until the disappearance of acidity, and recrystallized from methyl alcohol. 154.185 g. (57% yield) of a yellow product having a melting point of 53° C–56° C and a purity of 80%, were obtained.

EXAMPLE 2

Preparation of 2,6-Dinitro-4-Trifluoromethyldichlorobenzene By the Present Method 795 g. of 4-trifluoromethylchlorobenzene were added by dropping, in 0.5 hours and under stirring, to a mixture containing 1380 g. of 90% $HNO_3$ and 7,850 g. of $H_2SO_4$ at 20% of $SO_3$, pre-heated to 50°–60° C. After having brought the temperature to 100° C, always under stirring, and after having maintained said temperature for 3 hours, the whole was heated, still under intense stirring, to 110° C for 1 hour. The mass was allowed to cool to 60°–75° C in 3 hours, and the slurry was poured onto 16,000 g. of ice and water. A yellow solid in the form of needles separated. It was collected by filtration, washed with 31,000 g. of cold water and dried at 60° C. 1,000 g. of 2,6-dinitro-4-trifluoromethylchlorobenzene having a melting point of 55°–56° C and a purity of 96% were obtained.

What is claimed is:

1. A one-step process for preparing 2,6-dinitro-4-trifluorochlorobenzene from 4-trifluoromethylchlorobenzene which comprises adding 4-trifluoromethylchlorobenzene to a 1:5 to 1:6 mixture of about 90% $HNO_3$ and $H_2SO_4$ at 20% of $SO_3$, at a molar ratio of nitric acid to 4-trifluorochlorobenzene of 4.5:1, heating the resulting mixture to about 100° C for 3 hours and thereafter to about 110° C for 1 hour, with continued stirring, allowing the temperature of the mass to decrease to about 60° C to 70° C over a period of about 3 hours without stirring, and mixing the slurry thus obtained with ice and water to precipitate the 2,6-dinitro-4-trifluorochlorobenzene.

2. The process of claim 1, in which the mixture of about 90% $HNO_3$ and $H_2SO_4$ at 20% of $SO_3$ is preheated to about 50° C to 60° C before adding the 4-trifluorochlorobenzene to said mixture.